United States Patent [19]

MacLeay et al.

[11] Patent Number: 4,824,884
[45] Date of Patent: Apr. 25, 1989

[54] CYCLIC ANHYDRIDE DERIVATIVES OF HYDRAZIDE FUNCTIONALIZED HINDERED AMINE LIGHT STABILIZERS

[75] Inventors: Ronald E. MacLeay; Robert T. Kazmierczak, both of Williamsville, N.Y.

[73] Assignee: Pennwalt Corporation, Philadelphia, Pa.

[21] Appl. No.: 84,533

[22] Filed: Aug. 12, 1987

[51] Int. Cl.$^4$ .............................................. C08K 5/34
[52] U.S. Cl. ....................................... 524/99; 524/103; 546/187; 546/200; 546/208; 546/242; 546/244; 546/245; 546/247
[58] Field of Search ................ 524/99, 103; 546/187, 546/200, 208, 242, 244, 245, 247

[56] References Cited

U.S. PATENT DOCUMENTS

| | | | |
|---|---|---|---|
| 3,018,250 | 1/1962 | Anderson et al. | 252/51.5 |
| 3,024,195 | 3/1962 | Drummond et al. | 252/51.5 |
| 3,282,052 | 8/1974 | Holt et al. | 546/244 |
| 3,412,111 | 11/1968 | Irwin et al. | 260/346.8 |
| 3,639,334 | 2/1972 | Holoch | 260/45.9 |
| 3,684,765 | 8/1972 | Matsui et al. | 524/103 |
| 3,896,146 | 7/1975 | Stephen | 524/103 |
| 3,896,147 | 7/1975 | Stephen | 524/99 |
| 3,899,491 | 8/1975 | Ramey et al. | 260/268 |
| 3,906,002 | 9/1975 | Stephen | 260/326 |
| 3,937,711 | 2/1976 | Cook | 524/103 |
| 3,956,312 | 5/1976 | Magdanyl et al. | 260/310 |
| 4,001,181 | 1/1977 | Ramey et al. | 524/99 |
| 4,045,404 | 8/1977 | Stephen | 260/45.8 |
| 4,053,615 | 10/1977 | Boyle et al. | 546/200 |
| 4,118,368 | 10/1978 | Soma et al. | 524/103 |
| 4,145,512 | 3/1979 | Urhan | 546/244 |
| 4,153,596 | 5/1979 | Oertel et al. | 524/102 |
| 4,191,683 | 3/1980 | Burnetti et al. | 544/130 |
| 4,223,147 | 9/1980 | Oertel et al. | 546/242 |
| 4,336,183 | 6/1982 | Nakahara et al. | 524/99 |
| 4,348,524 | 9/1982 | Karrer et al. | 546/187 |
| 4,356,307 | 10/1982 | Kelkenberg et al. | 546/200 |
| 4,388,471 | 6/1983 | Wollenberg | 549/255 |
| 4,446,264 | 5/1984 | Cottman | 524/109 |
| 4,450,281 | 5/1984 | Wollenberg | 549/255 |
| 4,578,472 | 3/1986 | Yoshimura | 546/188 |
| 4,618,634 | 10/1986 | Cantatore et al. | 524/97 |
| 4,692,486 | 11/1987 | Gugumu | 524/100 |
| 4,730,017 | 3/1988 | Avar | 524/103 |
| 4,778,837 | 10/1988 | Waterman et al. | 524/103 |

FOREIGN PATENT DOCUMENTS

| | | |
|---|---|---|
| 1022296 | 12/1977 | Canada . |
| 1180496 | 1/1985 | Canada . |
| 0116517 | 1/1984 | European Pat. Off. . |
| 62-253657 | 11/1987 | Japan . |
| 2174093 | 10/1986 | United Kingdom . |

OTHER PUBLICATIONS

*Encyclopedia of Polymer Science and Engineering*, John Wiley & Sons Publ., 2nd Ed., 2:83–84 (N.D.).
W. B. Lutz, et al., *J. Org. Chem.*, 27:1695–1703 (1962).
J. C. S. Perkin II, pp. 533–535, (1977).

*Primary Examiner*—Veronica P. Hoke
*Attorney, Agent, or Firm*—Panitch Schwarze Jacobs and Nadel

[57] ABSTRACT

Amic acids, cyclic imides and mixtures thereof which contain both diacyl hydrazide functionalities and hindered amine functionalities are prepared by reacting non-halogenated cyclic anhydrides with hindered amine light stabilizers containing reactive hydrazido funtionalities in inert solvents or in inert polymeric compositions in a melt blending step. The compositions protect polymeric compositions against the degradative effects of heat and light.

23 Claims, No Drawings

CYCLIC ANHYDRIDE DERIVATIVES OF HYDRAZIDE FUNCTIONALIZED HINDERED AMINE LIGHT STABILIZERS

BACKGROUND OF THE INVENTION

This invention relates to amic acids, cyclic imides and mixtures thereof which contain both diacyl hydrazide functionalities and hindered amine light stabilizing functionalities. The invention also relates to the stabilization of polymers or copolymers against the deleterious effects of heat and/or light by the addition of an effective amount of one or more of the compounds. The invention also relates to the stabilization of polymeric compositions by incorporating the amic acid derivatives into the polymeric composition and then heating the polymeric composition in a melt blending step at a temperature above which cyclization of the amic acid to the cyclic imide occurs.

Synthetic polymers such as polyolefins (e.g., polyethylene and polypropylene), styrenics (e.g., polystyrene, rubber modified polystyrene, ABS, etc.), polyvinyl chloride, polycarbonates, polyesters, and polyphenylene ethers, to name a few, are subject to degradation and discoloration upon exposure to heat and/or light with consequent deterioration of mechanical and other properties.

Various stabilizers have been proposed to inhibit such deterioration. Hindered polyalkylpiperidine compounds have found extensive use in the photostabilization of polyolefins. Hydrazides have been used to prevent deterioration of polyolefins by heat, oxidation or heavy metal contamination. Derivatives of hydrazides are also commercially available for use as polymer stabilizers (See Encyclopedia of Polymer Science and Engineering, 2nd Ed. Vol 2. pp 83-84).

In addition to activity as a stabilizer, commercially useful stabilizer additives must have both excellent compatibility with and/or solubility in the polymeric substrate to be stabilized along with superior resistance to loss from the stabilized composition during processing and end-use application. Many stabilizer additives exhibit limited compatibility in certain substrates and excessive tendency to exude, sublime and/or volatilize during weathering or processing of the stabilized compositions. Therefore, it is highly desirable to provide stabilizers that have a high affinity of compatibility with the polymeric compositions to be stabilized.

Prior to the present invention, the results obtained with the known hindered amine light stabilizers have not been fully satisfactory with all types of manufactured articles, either from a stabilization, compatibility, volatility, exudability or economic viewpoint or combinations thereof. Therefore, further improvement in the field of hindered amine light stabilizers is still desirable.

The hydrazido functionalized polyalkylpiperidine starting materials have good light stabilizing properties but they are water soluble and would be readily leached out of the polymeric compositions to be stabilized if the polymeric compositions came in contact with water, steam, or aqueous solutions. Thus, they are not useful themselves in the stabilization of most polymeric compositions without being derivatized.

Cyclic imides containing polyalkylpiperidine moieties have been prepared by reacting cyclic anhydrides with 4-amino-2,2,6,6-tetramethylpiperidine. The imides were prepared by heating the anhydride and the amine in an autoclave at 200°-230° C. for several hours. No mention was made of the corresponding amic acids but the high temperatures employed were obviously used to cyclize the amic acid to the imide since the amine reacts readily with the anydrides at low temperatures (U.S. Pat. No. 4,356,307).

Amic acids were prepared by reacting cyclic anhydrides with 4-amino-2,6,6,6-tetramethylpiperidine at lower temperatures of 40°-140° C. (U.S. Pat. No. 4,001,181).

Amic acids were obtained by reacting cyclic anhydrides with 4-amino-2,2,5,6,6-polyalkylpiperidines. The amic acids were cyclized to the imides with acetic anhydride (U.S. Pat. No. 4,191,683).

U.S. Pat. No. 3,684,765 discloses phthalimide derivatives of 4-amino-2,2,6,6-tetramethylpiperidine. Canadian Patent No. 1,022,296 discloses phthalimide derivatives of 4-amino-1-ethoxycarbonylmethyl-2,2,6,6-tetramethylpiperidine.

All of the above mentioned prior art compounds were prepared from 4-amino-polyalkylpiperidines. None were prepared from hydrazido functionalized polyalkylpiperidines as in the present invention.

SUMMARY OF THE INVENTION

This invention is directed to a composition having the following structure:

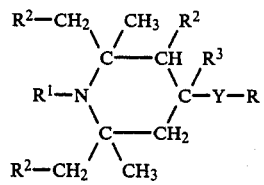

wherein R is selected from

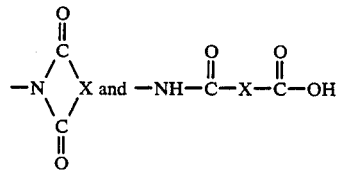

where X is a diradical of 2 to 200 carbons which is selected from:

1,2-aryl diradicals of 6-12 carbons, 1,8-naphthyl diradicals of 10-14 carbons, aryl-alkyl diradicals of 7-13 carbons, saturated or unsaturated alkylene, cycloalkylene or bicycloalkylene diradicals of 2-20 carbons all of which may be optionally substituted with carboxy, alkyl, of 1 to 40 carbons, alkylthio or alkoxy groups of 1 to 18 carbons, alkenyl of 2 to 40 carbons, arylthio of 6 to 20 carbons, aryl of 6 to 16 carbons, aralkyl of 7 to 17 carbons, aryloxy of 6 to 16 carbons, aralkylthio of 7 to 20 carbons or alkoxycarbonylalkylthio of 3 to 30 carbons.

$R^1$ is hydrogen, oxyl, hydroxyl, alkyl of 1 to 20 carbons, alkenyl or alkynyl of 3 to 8 carbons, aralkyl of 7 to 12 carbons, aliphatic acyl of 1 to 10 carbons, aromatic acyl of 7 to 13 carbons, alkoxycarbonyl of 2 to 9 carbons, aryloxycarbonyl of 7 to 15 carbons, alkyl, aryl, cycloalkyl or aralkyl substituted carbamoyl of 2 to 13 carbons, hydroxyalkyl of 1 to 5 carbons, 2-cyanoethyl, epoxyalkyl of 3 to 10 carbons or polyalkylene oxide of 4 to 30 carbons.

$R^2$ is hydrogen or alkyl of 1 to 4 carbons.

$R^3$ is hydrogen, hydroxyl or alkoxy of 1 to 4 carbons.

When $R^3$ is hydrogen, Y is a divalent radical selected from

—Z—$R^4$—C(=O)—N($R^5$)—, —Z—C(=O)—N($R^5$)—,

—Z—C(=O)—$R^6$—C(=O)—N($R^5$)—, —$R^4$—C(=O)—N($R^5$)—, and

—C(=O)—N($R^5$)—; Z is —O—, —N($R^7$)—, or —N($R^9$)—$R^8$—N($R^9$)—.

(N.B. In the definitions of Y, the orientation of the diradical is such that the hindered amine group is connected to the left end of the diradical and the R group is connected to the right end of the diradical).

When $R^3$ is hydroxyl or alkoxy, Y is a divalent radical selected from —$R^4$—C(=O)—N($R^5$)— and —C(=O)—N($R^5$).

$R^4$ is an alkylene diradical of 1–4 carbons.

$R^5$ is hydrogen, primary or secondary alkyl of 1–8 carbons, aralkyl of 7–12 carbons, or cycloalkyl of 5–10 carbons.

$R^6$ is a direct bond, alkylene of 1–14 carbons, oxydialkylene of 4–10 carbons, thiodialkylene of 4–10 carbons, alkenylene of 2–20 carbons, of o-, m-, or p-phenylene. Substituents for $R^6$ may be lower alkyl or lower alkoxy of 1–8 carbons, hydroxy, bromine, chlorine, mercapto or lower alkylmercapto of 1–8 carbons.

$R^7$ is hydrogen, alkyl of 1–10 carbons, aryl of 6–12 carbons, aralkyl of 7–12 carbons, cycloalkyl of 5–12 carbons, 2-cyanoethyl or a radical of the formula

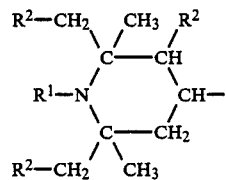

$R^8$ is alkylene of 2–12 carbons.

$R^9$ is hydrogen, alkyl of 1–10 carbons, aryl of 6–12 carbons, aralkyl of 7–12 carbons or cycloalkyl of 5–12 carbons.

Preferably, R is

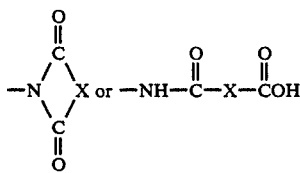

and X is o-phenylene, 1,2-ethylene, 1,3-propylene, 1,2-cyclohexylene, 4-methyl-1,2-cyclohexylene, 1,2-cyclohex-4-enylene, norborn-5-enylene, 2,3-norbornylene, 2,3-bicyclo[2.2.2]-oct-5-enylene, 2,3-bicyclo[2.2.2]octylene, higher alkyl, alkenyl, alkylthio, arylthio or aralkylthio substituted 1,2-ethylene or 2,3-norbornylenes.

$R^1$ is hydrogen, methyl, acetyl, benzoyl, 2-hydroxyethyl or benzyl, $R^2$ is hydrogen or methyl, $R^3$ is hydrogen, Y is a diradical selected from —Z—$R^4$—C(=O)—N($R^5$)— or —Z—C(=O)—$R^6$—C(=O)—N($R^5$)—

Z is —N($R^7$)—, $R^3$ and $R^5$ are hydrogen, $R^4$ is —(CH$_2$)$_b$— $R^6$ is a direct bond or alkylene or 1 to 4 carbons and b is 1 or 2 and $R^7$ is hydrogen or a 2,2,6,6-tetramethyl-4-piperidinyl radical.

DETAILED DESCRIPTION OF THE INVENTION

This invention is directed to a class of amic acids, cyclic imides, and mixtures thereof which contain both diacyl hydrazide (or N-(acylamino)imide) functionalities and hindered polyalkylpiperidine light stabilizing functionalities. The diacyl hydrazide functionality provides antioxidant and metal deactivating properties to the compounds while the hindered polyalkylpiperidine functionality provides light stabilizing properties to the compounds. The compositions of this invention are effective stabilizers for polymer compositions which are susceptible to the deleterious effects of heat, light or heavy metal contamination.

The compositions of this invention are prepared by reacting non-halogenated cyclic anhydrides with hindered amine light stabilizers containing reactive (i.e., the terminal nitrogen of the hydrazide functionality is unsubstituted) hydrazide functionalities. The amic acids are prepared by running the reaction at lower temperatures while the cyclic imides are prepared at higher temperatures or by cyclizing the amic acids at higher temperature or by standard dehydration methods (e.g., acetic anhydride and sodium acetate). The cyclization of the amic acid to the cyclic imide may be carried out neat, in a solvent or in a polymeric composition in a melt blending step such as an extrusion or compounding step.

Preferably, the composition of the instant invention is present in the cyclic imide form in the final polymeric composition.

Preferably, the cyclic anhydride has alkyl substituents which help increase the compatibility of the final product and decrease its volatility. Preferably, the hydrazido functionalized polyalkylpiperidine is a derivative of oxalic acid.

Examples of the composition of this invention include the following non-limiting list 1. N-(1,2,2,6,6-pentamethyl-4-piperidinyl)-N'-phthalimidosuccinamide, 2. N-(1-acetyl-2,2,6,6-tetramethyl-4-piperidinyl)-N'-(hexahydro-4'-methylphthalimido)adipamide, 3. N-(1-benzyl-2,2,6,6-tetramethyl-4-piperidinyl)-N'-(2-octadecylsuccinimido)malonamide, 4. N-(2,2,6,6-tetramethyl-4-piperidinyl)-N'-(5-norbornene-2,3-dicarboximido)oxamide, 5. N-(1-acetyl-2,2,6,6-tetramethyl-4-piperidinyl)-N'-(5-norbornene-2,3-dicarboximido)succinamide, 6. 3-(2,2,6,6-tetramethyl-4-piperidinylamino)-N-(2-octadecen-1-ylsuccinimido)propionamide, 7. 2-(1-benzoyl-2,2,6,6-tetramethyl-4-piperidinylamino)-N-(4-methylphthalimido)acetamide, 8. 3-(2,2,6,6-tetramethyl-4-piperidinylamino)-N-(5-norbornene-2,3-dicarboximido)propionamide, 9. N-(1-allyl-2,2,6,6-tetramethyl-4-piperidinyl)-N'-phthalimido-urea, 10. N-(1-octyl-2,2,6,6-tetramethyl-4-piperidinyl)-N'-(2-carboxybenzoylamino)oxamide, 11. 2,2,6,6-tetramethyl-4-piperidinyl N-phthalimidocarbamate, 12. N-(2,6-diethyl-2,3,6-trimethyl-4-piperidinyl)-N'-(2-dodecylsuccinimido)oxamide, 13. N-(2,2,6,6-tetramethyl-4-piperidinyl)-N'-(2-polybutadienylsuccinimido)oxamide, 14. N-(1-ethoxycarbonyl-2,2,6,6-tetramethyl-4-piperidinyl)-N'-(2-polyisobutylenylsuccinimido)oxamide, 15. N-(1,2,2,6,6-pentamethyl-4-piperidinyl)-N'-glutarimidooxamide, 16. N-(2,2,6,6-tetramethyl-4-piperidinyl)-N'-(bicyclo[2.2.2]oct-5-ene-2,3-dicarboximido)succinamide, 17. N-(2,2,6,6-tetramethyl-4-piperidinyl)-N'-(bicyclo[2.2.2]octane-2,3-dicarboximido)oxamide, 18. N-(2,2,6,6-tetramethyl-4-piperidinyl)-N'-[2-(3,5-di-t-butyl-4-hydroxyphenylthio)succinimido]oxamide, 19. N-(2,2,6,6-tetramethyl-4-piperidinyl)-N'-(2-dodecylthiosuccinimido)adipamide, 20. N-(2,2,6,6-tetramethyl-4-piperidinyl)-N'-[5-(dodecylthio)norbornane-2,3-dicarboximido]oxamide, 21. 3-(2,2,6,6-tetramethyl-4-piperidinyl)-N'-[5-benzylthio)norbornane-2,3-dicarboximido]propionamide, 22. N-(2,2,6,6-tetramethyl-4-piperidinyl)-N'-[5-(3,5-di-t-butyl-4-hydroxyphenylthio)bicyclo[2.2.2]octane-2,3-dicarboximido]oxamide, 23. N-(2,2,6,6-tetramethyl-4-piperidinyl)-N'-[5-(3,5-di-t-amyl-4-hydroxybenzylthio)bicyclo[2.2.2]octane-2,3-dicarboximido]succinamide, 24. N-(2,2,6,6-tetramethyl-4-piperidinyl)-N'-[2-(3,5-di-t-butyl-4-hydroxyphenylthio)-3-carboxypropionylamino]oxamide, 25. N-(2,2,6,6-tetramethyl-4-piperidinyl)-N'-[4-(3,5-di-t-butyl-4-hydroxyphenylthio)-1,2-cyclohexanedicarboximiod]oxamide, 26. N,N-bis(2,2,6,6-tetramethyl-4-piperidinyl)-N'-(2-dodecen-1-ylsuccinimido)propionamide, and 27. 3-[N,N-bis(2,2,6,6-tetramethyl-4-piperidinyl)amino]-N-(2-dodecen-1-ylsuccinimido)propionamide.

The composition of this invention is an effective additive for the stabilization of polymeric compositions which are normally subject to thermal, oxidative or actinic light degradation. At times it may be beneficial to add extraneous additives which will act as synergists with the hindered amine light stabilizing groups.

The composition of this invention can be blended with various polymeric compositions in high concentrations to form masterbatches which can then be blended with additional polymer either of the same or different type.

The amount of stabilizer composition used to stabilize the polymeric composition will depend on the particular polymer system to be stabilized, the degree of stabilization desired and the presence of other stabilizers in the composition. Normally it is advisable to have about 0.01 to about 5% by weight of the 2,2,6,6-tetraalkylpiperidine moiety present in the polymeric composition. An advantageous range is from about 0.05 to about 2% by weight of the 2,2,6,6-tetraalkylpiperidine portion of the molecule in the final composition; in most cases, 0.1 to about 1% by weight is sufficient. Preferably the composition of the present invention is in the cyclic imide form in the final state of the stabilized polymeric composition.

Examples of polymeric compositions which may be stabilized by the hindered amine light stabilizer composition of the present invention include:

1. Polyolefins such as high, low and linear low density polyethylenes, which may be optionally crosslinked, polypropylene, polyisobutylene, poly(methylbutene-1), polyacetylene and in general polyolefins derived from monomers having from two to about ten carbon atoms and mixtures thereof.

2. Polyolefins derived from diolefins such as polybutadiene and polyisoprene.

3. Copolymers of mono or diolefins such as ethylene-propylene, propylene-butene-1, propylene-isobutylene and ethylene-butene-1 copolymer.

4. Terpolymers of ethylene and propylene with dienes (EPDM) such as butadiene, hexadiene, dicyclopentadiene and ethylene-butene-1.

5. Copolymers of alpha-olefins with acrylic acid or methacrylic acids or their derivatives such as ethylene-acrylic acid, ethylene-methacrylic acid and ethylene-ethyl acrylate copolymers.

6. Styrenic polymers such as polystyrene (PS) and poly(p-methylstyrene).

7. Styrenic copolymers and terpolymers such as styrene-butadiene (SBR), styrene-allyl alcohol and styrene-acrylonitrile (SAN), styrene-acrylonitrilemethacrylate terpolymer, styrene-butadiene-styrene block copolymers (SBS) rubber modified styrenics such as styrene-acrylonitrile copolymers modified with acrylic ester polymer (ASA), graft copolymers of styrene on rubbers such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers such as butadiene (ABS), polyisoprene or styrene-butadiene-styrene block copolymers, graft copolymers of styrene-methyl methacrylate on rubbers such as polybutadiene (MBS), butadiene-styrene radial block copolymers (e.g., KRO 3 of Phillips Petroleum Co.), selectively hydrogenated butadiene-stryene block copolymers (e.g., Kraton G from Shell Chemical Co.) and mixtures thereof.

8. Polymers and copolymers derived from halogen-containing vinyl monomers such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride-vinyl acetate copolymers and ethylene-tetrafluoroethylene copolymers.

9. Halogenated rubbers such as chlorinated and/or brominated butyl rubbers or polyolefins and fluoroelastomers.

10. Polymers and copolymers derived from alpha, beta-unsaturated acids, anhydrides, esters, amides and nitriles or combinations thereof such as polymers or copolymers of acrylic and methacrylic acids, alkyl and/or glycidyl acrylates and methacrylates, acrylamide and methacrylamide, acrylonitrile, maleic anhydride, maleimide, the and copolymers of the above polymers and various blends and mixtures thereof as well as rubber modified versions of the above polymers and copolymers.

11. Polymers and copolymers derived from unsaturated alcohols or their acylated derivatives such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.

12. Polymers and copolymers derived from unsaturated amines such as poly(allyl melamine).

13. Polymers and copolymers derived from epoxides such as polyethylene oxide, polypropylene oxide and copolymers thereof as well as polymers derived from bis-glycidyl ethers.

14. Poly(phenylene oxides), poly(phenylene ethers) and modifications thereof containing grafted polystyrene or rubbers as well as their various blends with polystyrene, rubber modified polystyrenes or nylon.

15. Polycarbonates and especially the aromatic polycarbonates such as those derived from phosgene and bisphenols such as bisphenol-A, tetrabromobisphenol-A, and tetramethylbisphenol-A.

16. Polyester derived from dicarboxylic acids and diols and/or hydroxycarboxylic acids or their corresponding lactones such as polyalkylene phthalates [e.g., polyethylene terephthalate (PET), polybutylene terephthalate (PET), and poly (1,4-dimethylcyclohexane terephthalate)] or copolymers thereof and polylactones such as polycaprolactone.

17. Polyarylates derived from bisphenols (e.g., bisphenol-A) and various aromatic acids such as isophthalic and terephthalic acids or mixtures thereof.

18. Aromatic copolyestercarbonates having carbonate as well as ester linkages present in the backbone of the polymers such as those derived from bisphenols, iso- and terephthaloyl chlorides and phosgene.

19. Polyurethanes and polyureas.

20. Polyacetals such as polyoxymethylenes and polyoxymethylenes which contain ethylene oxide as a comonomer.

21. Polysulfones, polyethersulfones and polyimidesulfones

22. Polyamides and copolyamides which are derived from diamines and dicarboxylic acids and/or from aminocarboxylic acids or the corresponding lactams such as the following nylons: 6, 6/6, 6/10, 11 and 12.

23. Polyimides, polyetherimides, polyamideimides and copolyetheresters.

24. Crosslinked polymers which are derived from aldehydes on the one hand and from phenols, ureas or melamine on the other hand such as phenolformaldehyde, urea-formaldehyde, and melamineformaldehyde resins.

25. Alkyl resins such as glycerol-phthalic acid resins and mixtures thereof with melamine-formaldehyde resins.

26. Blends of vinyl monomers and unsaturated polyester resins which are derived from copolyesters of saturated and unsaturated dicarboxylic acids with polyhydric alcohol as well as from vinyl compounds (crosslinking agents) and also halogen-containing, flame resistant modifications thereof.

27. Natural polymers such as cellulose, natural rubber as well as the chemically modified homologous derivatives thereof such as cellulose acetates, cellulose propionate, cellulose butyrate and the cellulose ethers such as methyl and ethyl cellulose.

In addition, the stabilizer composition of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber-modified styrenics or nylon.

The hindered amine light stabilizer compostion of this invention can be used together with other additives to further enhance the properties of the finished polymer. Examples of other additives that can be used in conjunction with the stabilizers of this invention include antioxidants such as alkylated monophenols, alkylated hydroquinones, hydroxylated thiodiphenyl ethers, alkylidene-bis-phenols, hindered phenolic benzyl compounds, acylaminophenols, esters of 2-(3,5-di-t-butyl-4-hydroxyphenyl)propionic acid, esters of 2-(5-t-butyl-4-hydroxy-3-methyl-phenyl)propionic acid, 2-(3,5-di-t-butyl-4-hydroxyphenyl)-propionic acid amides, hydroxylamine derivatives such as N,N-dibenzylhydroxylamine, UV absorbers and light stabilizers such as 2-hydroxyphenyl)-2H-benzotriazoles, 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers; other additives such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and non-dripping agents, melt flow improvers and antistatic agents. Numerous examples of suitable additives of the above type are given in Canadian Pat. No. 1,190,038.

GENERAL PREPARATIVE METHODS

The hindered amine light stabilizers of this invention are prepared by reacting hindered amine light stabilizers bearing a reactive hydrazide functionality with cyclic hydrocarbyl anhydrides. Hydrocarbyl, as used in describing the cyclic anhydrides, denotes an organic radical composed of carbon and hydrogen which may be aliphatic, alicyclic, bicyclic, aromatic or combinations thereof, e.g., aralkyl. The hydrocarbyl backbone may be optionally substituted with alkyl groups of 1 to 40 carbons or alkenyl groups of 2–40 carbons, aryl groups of 6–12 carbons, aralkyl groups of 7–13 carbons, hydroxy, mercapto, alkyl or arylmercapto, carboxy, alkoxycarbonyl, alkoxy groups or polyalkyleneoxy groups.

The hydrazide group of the stabilizer reacts with the cyclic anhydride to form an amic acid containing an acylamino substituent on the amide nitrogen of the amic acid. If the amic acid is heated sufficiently, further reaction occurs in which a molecule of water is lost and a ring is formed with two carbonyl groups attached to the amide nitrogen. The cyclized product is a cyclic imide and in this case is more accurately described as a cyclic N-(acylamino)imide.

Depending upon the structure of the anhydride and the hydrazido functionalized hindered amine, the formation of the amic acid and its cyclization to the N-(acylamino)imide occurs under a wide range of reaction conditions, particularly reaction temperature and duration. Temperature is usually the dominant factor. Below a certain temperature (about 100° C.) the amic acid will not convert to the imide in an appreciable extent without the aid of a dehydrating agent, e.g., acetic anhydride, acid catalyst, etc. Above a certain temperature (about 120°-200° C. depending on structure), an amic acid, once formed, will predominantly cyclize to the imide. The imidization temperature for any particular amic acid can readily be determined by running a DSC (differential scanning calorimeter) scan under nitrogen. An endothermic peak is generated when the imidization occurs.

Many of the amic acids of this invention cyclize to the N-(acylamino)imide at relatively low temperatures e.g., in refluxing xylene (135°-140° C.).

The reaction of the hydrazido functionalized polyalkylpiperidines with the cyclic hydrocarbyl anhydrides may be carried out in inert solvents such as toluene, xylene, chlorobenzene, mesitylene, dimethylformamide, dimethylacetamide, tetrahydrofuran, and N-methyl-2-pyrrolidone. In some cases the reaction may be run in hot water. The reaction may also be carried out in a melt blending step either neat or in an inert polymeric composition. This can be accomplished at a temperature above the softening point of the polymeric composition using any conventional melt mixing apparatus such as a plastograph, Banbury mixer, two roll mill, single or twin screw extruder or any other method which applied sufficient heat (e.g., 150° to 300° C.) and shear to the ingredients to obtain a satisfactory molten blend. Preferably, the reaction is carried out in an inert atmosphere such as nitrogen. The polymeric compositions should be void of anhydride, epoxy, hydroxyl, thio or amino groups to prevent the reactants from reacting with the polymeric composition. Examples of suitable inert polymeric compositions the reaction can be run in include polystyrene, rubber-modified polystyrene, halogenated polystyrenes, polyolefins such as polyethylene, polypropylene, copolymers thereof, ABS, SAN, MBS, ASA, poly-(phenylene oxide), poly-(phenylene ethers) and various combinations thereof. Preferably, only the conversion of the amic acid to the more compatible cyclic imide is carried out in the polymeric composition. The reaction may be carried out for times varying from 30 seconds to 48 hours depending upon the degree of conversion of the anhydride to the imide desired, the reactivity of the functionalized hindered amine light stabilizers, the reaction temperature employed, the presence or absence of a solvent and the use or non-use of a catalyst. Higher reaction temperatures naturally reduce the required reaction time for any particular systems of reactants. Preferably, the reactions are carried out at temperatures between 125° and 225° C.

When the reactions are run in solution, the products are normally isolated by removal of solvent. In the case of insoluble products or slightly soluble products, the solvent is removed by filtration, preferably warm. In the case of soluble products, the solvent is removed from the product by evaporation such as on a rotating evaporator under reduced pressure.

STARTING MATERIALS (A) Hydrazido Functionalized Hindered Amine Light Stabilizers Most of the hydrazido functionalized hindered amine light stabilizers used as starting materials for the preparation of the compositions of this invention are derivatives of 4-amino-2,2,6,6-tetraalkylpiperidines. The 4-amino-2,2,6,6-tetraalkylpiperidines are usually prepared by the reductive amination of 2,2,6,6-tetraalkylpiperidones with ammonia or primary amines [See U.S. Pat. No. 4,191,683 or W. B. Lutz, S. Lazarus and R. I. Meltzer, J. Org. Chem. 27,1695 (1962)]. 4-Amino-2,2,6,6-tetramethylpiperidine, N-butyl-triacetonediamine and bis-(2,2,6,6-tetramethyl-4-piperidyl)amine are available from Huls Chemische Werke in Germany.

Prior to the reductive amination, alkyl, alkenyl, alkynyl, aralkyl, hydroxyalkyl or 2-cyanoethyl groups may be introduced on the hindered nitrogen by standard alkylation techniques using alkyl, alkenyl, alkynyl or aralkyl halides, dialkyl sulfates, alkylene oxides or acrylonitrile. Alternatively, the 4-amino-2,2,6,6-tetraalkylpiperidine may be converted to the corresponding 4-benzoylamino-2,2,6,6-tetraalkylpiperidine, the hindered amine alkylated with one of the above alkylating agents and then the benzoyl group hydrolyzed with concentrated hydrochloric acid. These techniques are demonstrated in U.S. Pat. No. 4,223,147.

The 4-amino-2,2,6,6-tetraalkylpiperidines or their 1-substituted derivatives may be reacted with an excess of a diester to form a monoamide-monoester which can then be reacted with hydrazine, hydrazine hydrate or a mono-substituted alkylhydrazine to form a hydrazido substituted hindered amine light stabilizer. The intermediate monoamide-monoesters may also be prepared by the reaction of the 4-amino-2,2,6,6-tetraalkylpiperidine with mono acid chlorides-mono esters of dicarboxylic acids or mono esters of dicarboxylic acids followed by esterification of the carboxyl group. Some may also be prepared by reaction with a cyclic anhydride of a 1,2 or 1,3-dicarboxylic acid followed by esterification of the carboxyl group. The intermediate monoamide-monoesters may be alkylated on the hindered nitrogen if it is unsubstituted with the above alkylating agents or acylated with aliphatic or aromatic acid chlorides, chloroformates, carbamoyl chlorides or isocyanates. The alkylation or acylation of the unsubstituted hindred nitrogen should be carried out prior to the conversion of the intermediate mono-amide-mono-ester to the hydrazide. These techniques are demonstrated in U.S. Pat. Nos. 4,348,524 and 4,191,683.

The 4-amino-2,2,6,6-tetraalkylpiperidines or their 1-substituted derivatives may be added to alkyl acrylates and methacrylates via Michael Addition to form 2,2,6,6-tetraalkyl-4-piperidinyl substituted propionates or 2-methyl-propionates which are then reacted with a hydrazine to form the corresponding hydrazide. Alkylation or acylation of the hindered nitrogen of the intermediate ester may be carried out if desired prior to the hydrazinolysis step. These techniques are also demonstrated in U.S. Pat. No. 4,223,147.

The semicarbazide derivatives are prepared by reacting the 4-amino-2,2,6,6-tetraalkylpiperidines or their 1-substituted derivatives with diphenyl carbonate and then reacting the resulting phenyl carbamate with a hydrazine. Again, substitution on the hindered nitrogen may be performed on the intermediate phenyl carbamate prior to the hydrazinolysis step. This technique is also demonstrated in U.S. Pat. No. 4,223,147.

Hydrazido functionalized hindered amine light stabilizers may also be prepared by reacting halo-substituted esters such as lower alkyl chloroacetates or bromopropionates with 4-amino or 4-hydroxy-2,2,6,6-tetra-alkylpiperidines to form the HALS substituted acetates or propionates (see U.S. Pat. Nos. 4,578,472 and 4,618,634) which are readily converted to the corresponding hydrazides with a hydrazine.

The carbazate derivatives are prepared by reacting a 4-hydroxy-2,2,6,6-tetraalkylpiperidine or a 1-substituted derivative with phosgene or phenyl chloroformate in the presence of a base to form the symmetrical carbonate or the phenyl carbonate respectively. Again, substitution on the hindered nitrogen (if unsubstituted) may be effected at this point if desired. Hydrazinolysis of the carbonate or the phenyl carbonate using little or no excess hydrazine will produce the 2,2,6,6-tetraalkyl-4-piperidinyl carbazate (or its 1-substituted derivative).

4-Hydroxy-2,2,6,6-tetramethylpiperidine-4-ol and 4-hydroxy-1,2,2,6,6-pentamethylpiperidine-4-ol are both available from Huls Chemisch Werke. Hydrazido functionalized hindered amine light stabilizers containing oxyl substituents on the hindered nitrogen are prepared by reacting the corresponding unsubstituted hindered nitrogen with a peracid or hydrogen peroxide in the presence of tungsten catalysts (See U.S. Pat. No. 4,348,524). The oxidation of the unsubstituted hindered amine to the oxyl radical is preferably carried out on the various intermediates prior to the hydrazinolysis step. The oxyl radical may be converted to a hydroxyl radical by catalytic hydrogenation in the presence of a noble metal or nickel catalyst or chemical reduction using zinc or borane.

Hindered amine light stabilizers bearing reactive hydrazido functionalities which may be reacted with the cyclic anhydrides include the following non-exclusive examples:

3-(2,2,6,6-tetramethyl-4-piperidinylamino)propionhydrazide, 3-(1,2,2,6,6-pentamethyl-4-piperidinylamino)propionhydrazide, (2,2,6,6-tetramethyl-4-piperidinylamino)acethylhydrazide, (1,2,2,6,6-pentamethyl-4-piperidinylamino)-acetylhydrazide, N-(2,2,6,6-tetramethyl-4-piperidinyl)hydrazinecarboxamide, N-(1,2,2,6,6-pentamethyl-4-piperidinyl)hydrazinecarboxamide, N-(2,2,6,6-tetramethyl-4-piperidinyl)-N'-aminooxamide, N-(1,2,2,6,6-pentamethyl-4-piperidinyl)-N'-aminooxamide, N-(2,2,6,6-tetramethyl-4-piperidinyl)-N'-aminosuccinamide, N-(1,2,2,6,6-pentamethyl-4-piperidinyl)-N'-aminosuccinamide, N-(2,2,6,6-tetramethyl-4-piperidinyl)-N'-aminomalonamide, N-(1-benzyl-2,2,6,6-tetramethyl-4-piperidinyl)-N'-aminomalonamide, N-(1-benzyl-2,2,6,6-tetramethyl-4-piperidinyl)-N'-aminooxamide, N-(2,6-diethyl-2,3,6-trimethyl-4-piperidinyl)-N'-aminoadipamide, N-(1-acetyl-2,2,6,6-tetramethyl-4-piperidinyl)-N'-aminooxide, 3-(1-acetyl-2,2,6,6-tetramethyl-4-piperidinylamino)-propionhydrazide, (2,2,6,6-tetramethyl-4-piperidinyloxy)acetyl hydrazide, (1,2,2,6,6-pentamethyl-4-piperidinyloxy)acetylhydrazide, 3-(2,2,6,6-tetramethyl-4-piperidinyloxy)propionhydrazide, 3,(1,2,2,6,6-pentamethyl-4-piperidinyloxy)propionhydrazide, N-(1-acetyl-2,2,6,6-tetramethyl-4-piperidinyl)hydrazine carboxamide, N-(1-benzoyl-2,2,6,6-tetramethyl-4-piperidinyl)-N'-aminooxamide, 3-(1-benzoyl-2,2,6,6-tetramethyl-4-piperidinylamino)propionyl hydrazide, N,N-bis(2,2,6,6-tetramethyl-4-piperidinyl)-N'-aminooxamide, 3-[N,N-bis(2,2,6,6-tetramethyl-4-piperidinyl)amino]-propionhydrazide, and 2-[N,N-bis(2,2,6,6-tetramethyl-4-piperidinyl)amino]acetyl hydrazide.

(B) Non-Halogenated Cyclic Anhydrides

Cyclic hydrocarbyl anhydrides which may be reacted with the hydrazido functionalized polyalkylpiperidines include the following non-exclusive examples:

phthalic, 4-methylphthalic, homophthalic, tetrahydro-4-methylphthalic, hexahydrophthalic, hexahyro-4-methylphthalic, hexahydro-3-methylphthalic, 1,8-naphthalic, trimellitic, camphoric, maleic, 2-methylmaleic, 2,3-dimethylmaleic, citraconic, itaconic, glutaric, 2-methylglutaric, 2,2-dimethylglutaric, 3-methylglutaric, 3,3-dimethylglutaric, 3,3-tetramethyleneglutaric, ciscyclohexene-1,2-dicarboxylic, succinic, 2-methyl succinic, 2,3-dimethylsuccinic, 2-dodecen-1-ylsuccinic, 2-dodecylsuccinic, 2-hexadecen-1-ylsuccinic, 2-hexadecylsuccinic, 2-octadecen-1-ylsuccinic and 2-octadecylsuccinic anhydrides.

Long chain 2-alkenyl or alkyl succinic anhydrides are particularly useful in increasing the compatibility of the stabilizer compositions of the present invention with polyolefins and simultaneously decreasing their volatility.

The alkenyl-substituted succinic anhydrides are generally prepared by reacting alpha-olefins with maleic anhydride at a temperature in the range of about 160° C. to about 240° C. Generally these reactions are conducted at atmospheric pressure although higher pressures can be used, particularly when the olefin has a relatively low molecular weight. The procedures for preparing these hydrocarbyl-substituted succinic anhydrides are well known to those skilled in the art and have been described, for example in U.S. Pat. No. 3,412,111 and in J. C. S. Perkin II, (1977), pp 533-5. Reduction of the alkenyl-substituted succinic anhydride yields the corresponding alkyl-substituted succinic anhydride. Many of the alkenyl and alkyl-substituted succinic anhydrides are available from Humphrey Chemical, North Haven, CT.

Cyclic anhydrides derived from Diels-Alder reactions of maleic anhydride and dienes such as butadiene, isoprene, piperylene, cyclopentadiene, trimethylcyclohexadiene, among others, and corresponding hydrogenated Diels-Alder products are also useful starting materials. Such anhydrides include the following non-exclusive examples:

5-norbornene-2,3-dicarboxylic anhydride,
norbornane-2,3-dicarboxylic anhydride,
bicyclo[2.2.2]oct-5-ene-2,3-dicarboxylic anhydride,
methyl-5-norbornene-2,3-dicarboxylic anhydride,
3,6-endoxo-1,2,3,6-tetrahydrophthalic anhydride,
4,6,6-trimethylbicyclo[2.2.2]oct-7-ene-2,3,dicarboxylic anhydride, and
bicyclo[2.2.2]octane-2,3-dicarboxylic anhydride.

In addition, the cyclic anhydrides derived from the addition of alkyl or arylthiols to the double bonds of maleic anhydride, 5-norbornene-2,3-dicarboxylic and bicyclo-[2.2.2]oct-5-ene-2,3-dicarboxylic anhydrides are also useful starting materials for this invention. U.S. Pat. Nos. 3,896,147 and 3,896,146 disclose the addition of alkylmercaptans and omega-mercaptoalkanols respectively to 5-norbornene-2,3-dicarboxylic and bicyclo[2.2.2]oct-5-ene-2,3-dicarboxylic anhydrides. U.S. Pat. No. 4,446,264 discloses the addition of thiols to the double bond of maleic anhydride in the presence of basic catalysts to produce 2alkylthio-succinic anhydrides. European Patent Application No. 0,116,517 discloses the addition of mercaptophenols (specifically dialkyl-4-hydroxythiophenols) to the double bond of maleic anhydride to produce 2-(dialkyl-4-hydroxyphenyl)thio-substituted succinic anhydrides.

Examples of such thio-substituted anhydrides which are useful starting materials for the compounds of this invention include the following non-exclusive list:

5-(2-hydroxyethylthio)-norbornane-2,3-dicarboxylic anhydride, 5-(6-hydroxyethylthio)norbornene-2,3-dicarboxylic anhydride, 5-(3-hydroxypropylthio)-bicyclo[2.2.2]octane-2,3-dicarboxylic anhydride, 5-(benzylthio)-norbornane-2,3-dicarboxylic anhydride, 5-(dodecylthio)norbornane-2,3-dicarboxylic anhydride, 5-(octadecylthio)-bicyclo[2.2.2]octane-2,3-carboxylic anhydride, 5-[(3,5-di-t-butyl-4-hydroxyphenyl)thio]norbornane-2,3-dicarboxylic anhydride, 5-[(3-t-butyl-5-methyl-4-hydroxyphenyl)thio]-norbornane-2,3-dicarboxylic anhydride, 5-[(3,5-di-t-butyl-4-hydroxyphenyl)thio]-bicyclo[2.2.2]-octane-2,3-dicarboxylic anhydride, 2-(2-hydroxyethylthio)-succinic anhydride, 2-(benzylthio)-succinic anhydride, 2-(octylthio)-succinic anhydride, 2-(dodecylthio)-succinic anhydride, 2-(hexadecylthio)-succinic anhydride, 2-[(3,5-di-t-butyl-4-hydroxyphenyl)thio]-succinic anhydride, 2-[(3-t-butyl-5-methyl-4-hydroxyphenyl)thio]-succinic anhydride, 2-[(3,5-di-t-butyl-4-hydroxy benzyl)thio]-succinic anhydride, 4-(dodecylthio)-cyclohexane-1,2-dicarboxylic anhydride 4-[(3,5-di-t-butyl-4-hydroxyphenyl)thio]-cyclohexane-1,2-dicarboxylic anhydride, and 4-[(3,5-di-t-amyl-4-hydroxybenzyl)thio]-cyclohexane-1,2-dicarboxylic anhydride.

The following hydrazido substituted hindered amine light stabilizers were used in the preparation of the compounds in the working examples.

N-(2,2,6,6-tetramethyl-4-piperidinyl)-N'-aminooxamide was prepared by reacting 4-amino-2,2,6,6-tetramethylpiperidine with an excess of diethyl oxalate, stripping off the unreacted diethyl oxalate and reacting the residue with 80% hydrazine hydrate in methanol.

3-(2,2,6,6-tetramethyl-4-piperidinylamino)propionhydrazide was prepared by the addition of 4-amino-2,2,6,6-tetramethylpiperidine to methyl acrylate followed by hydrazinolysis of the resultant ester. A detailed description can be found in U.S. Pat. No. 4,223,147.

N-(2,2,6,6-tetramethyl-4-piperidinyl)-N'-aminosuccinamide was prepared by the reaction of 4-amino-2,2,6,6-tetramethyl-piperidine with ethyl succinoyl chloride and hydrazinolysis of the resultant ester with 90% hydrazine hydrate in methanol.

EXAMPLE I

Reaction of 2-Dodecen-1-ylsuccinic Anhydride with N-(2,2,6,6-tetramethyl-4-piperidinyl)-N'-aminooxamide (A) In Tetrahyrofuran at 35° C.

Into a 250 ml 3-neck round bottom flask were added 13.35 grams (0.05 mole) of 2-dodecen-1-ylsuccinic anhydride and 150 ml of tetrahydrofuran. The flask was equipped with a magnetic stirrer, thermometer and reflux condenser. The mixture was warmed to 35° C. with stirring in a water bath and then 12.1 grams (0.05 mole) of N-(2,2,6,6-tetramethyl-4-piperidinyl)-N'-aminooxamide were added over about 5 minutes. A white precipitate formed quite readily. The reaction mixture was stirred approximately 2 hours allowing the temperature to drop back to room temperature. The precipitate that formed was difficult to filter so the tetrahydrofuran was stripped off on a rotating evaporator under reduced pressure. The residue was scraped out of the flask and pulverized in a mortar with a pestle. The white solid weighed 22.6 grams. The product melted at 168°–172° C. The infrared spectrum (nujol mull) of the product had a strong broad carbonyl band at 1610–1635 cm$^{-1}$ and a weaker band at 1520–1540 cm$^{-1}$. The carbonyl of the starting anhydride at 1755 cm$^{-1}$ had completely disappeared. The infrared spectrum was consistent with the amic acid structure indicating the product was predominantly N-(2,2,6,6-tetramethyl-4-piperidinyl)-N'-[3-carboxy-2(dodecen-1-yl)propionylamino]oxamide.

(B) In Refluxing Xylene

Into a 250 ml 3-neck round bottom flask were added 13.35 grams (0.05 mole) of 2-dodecen-1-ylsuccinic anhydride and 150 ml of xylene. The flask was equipped with a magnetic stirrer, thermometer and Dean Stark trap containing a reflux condenser. The mixture was heated to 140° C. and then 12.1 grams (0.05 mole) of N-(2,2,6,6-tetramethyl-4-piperidinyl)-N'-aminooxamide were added over about 15 minutes. The reaction mixture was then azeotroped for 3 hours at 139°–141° C. The reaction mixture was cooled, transferred to a 500 ml round bottom flask and the xylene was stripped off on a rotating evaporator under reduced pressure. The residue weighed 20.2 grams. The warm molten product was draind out of the flask onto a watch glass to harden. After solidifying, the residue was pulverized in a mortar with a pestle. The cream colored solid melted at 60°–64° C. The infrared spectrum of the product had sharp carbonyl bands at 1740 cm$^{-1}$ and 1680 cm$^{-1}$ and a weaker band at 1610 cm$^{-1}$. The infrared spectrum of the product was consistent with the imide structure indicating that ring closure had occurred and the product was predominantly N-(2,2,6,6-tetra-methyl-4-piperidinyl)-N'-(2-dodecen-1-ylsuccinimido)oxamide.

EXAMPLES IIA–VIIA

The compounds of Examples IIA–VIIA were prepared in tetrahydrofuran using the procedure of Example IA and substituting 0.05 moles of the appropriate anhydride for the 2-dodecen-1-ylsuccinic anhydride. The insoluble products were isolated by filtration and air dried. The infrared spectra (nujol mull) of the products were all consistent with the amic acid structure indicating that cyclization to the imide had not occurred. The results are summarized in Table I.

EXAMPLES IIB–VIIB

The compounds of Examples IIB–VIIB were prepared in refluxing xylene using the procedure of Example IB and substituting 0.05 moles of the appropriate anhydride for the 2-dodecen-1-yl anhydride. The insoluble products were isolated by filtration, washed with hexane to remove residual xylene, and air dried. Soluble products were isolated by stripping off the xylene on a rotating evaporator under reduced pressure. Infrared spectra were run on the products to determine if they were predominantly the acmic acid or the imide. The results are summarized in Table II.

TABLE I

Reaction of N—(2,2,6,6-tetramethyl-4-piperidinyl)-
N'—aminooxamide with Cyclic Anhydrides in Tetrahydrofuran

| Ex. # | Anhydride | Grams Anhydride | Yield (grams) | Color | m.p. °C. | Carbonyl Bands (cm$^{-1}$) | Intensity |
|---|---|---|---|---|---|---|---|
| IIA | glutaric | 5.71 | 17.9 | white | 212–214 | 1650 | strong |
| | | | | | | 1570–1610 | medium |
| IIIA | hexahydro-4-methyl phthalic | 8.41 | 19.6 | white | 160–163 | 1620 | strong |
| | | | | | | 1640 | strong |
| | | | | | | 1490–1530 | weak |
| IVA | methyl-5-norbornene-2,3-dicarboxylic | 8.91 | 23.6 | lt. yellow | 145–147 | 1660 | strong |
| | | | | | | 1630 | strong |
| | | | | | | 1590 | weak |
| | | | | | | 1530 | weak |
| VA | phthalic | 7.41 | 20.0 | white | >300 | 1630 | strong |
| | | | | | | 1670 | weak |
| | | | | | | 1530–1550 | weak |
| VIA | succinic | 5.0 | 17.5 | white | 243–246 | 1640 | strong |
| | | | | | | 1500–1530 | medium |
| VIIA | 2-octadecenyl | 17.5 | 26.2 | tan | 195–215 | 1665 | medium |
| | | | | | | 1630 | strong |
| | | | | | | 1615 | strong |
| | | | | | | 1530 | medium |

TABLE II

REACTION OF N—(2,2,6,6-TETRAMETHYL-4-PIPERIDINYL)-
N'—AMINOOXAMIDE WITH CYCLIC ANHYDRIDES
IN REFLUXING XYLENE

| EXAMPLE # | ANHYDRIDE | GRAMS | YIELD* insol | YIELD* sol | COLOR | MP C. | IR (Vc = o) | INTENSITY | MAJOR PRODUCT |
|---|---|---|---|---|---|---|---|---|---|
| IIB | GLUTARIC | 5.71 | 15.4 | — | WHITE | 217–220 | 1650 | STRONG | AMIC |
| | | | | | | | 1610 | WEAK | ACID |
| | | | | 1.5 | WHITE | 179–182 | 1710 | STRONG | IMIDE |
| | | | | | | | 1670 | STRONG | |
| IIIB | HEXAHYDRO 4-METHYL PHTHALIC | 8.41 | 20.6 | — | WHITE | 125–128 | 1740 | STRONG | IMIDE |
| | | | | | | | 1680 | STRONG | |
| | | | | | | | 1610 | MEDIUM | |
| IVB | METHYL-5-NORBORNENE 2,3-DICARBOXYLIC | 8.91 | 16.3 | — | WHITE | 140–142 | 1685 | STRONG | AMIC |
| | | | | | | | 1600 | MEDIUM | ACID |
| | | | | 5.0 | WHITE | 110–112 | 1735 | STRONG | IMIDE |
| | | | | | | | 1680 | MEDIUM | |
| | | | | | | | 1615 | STRONG | |
| VB | PHTHALIC | 7.41 | 19.6 | — | | >300 | 1740 | WEAK | AMIC |
| | | | | | | | 1635 | STRONG | ACID |
| | | | | | | | 1540 | MEDIUM | |
| | | | | 0.4 | WHITE | 185–187 | 1740 | MEDIUM | IMIDE |
| | | | | | | | 1665 | STRONG | |
| VIIB | 2-OCTADECENYL | 17.5 | — | 30. | TAN | — | 1730 | STRONG | IMIDE |
| | | | | | | | 1670 | STRONG | |

* = ISOLATED FROM XYLENE, SEE EXAMPLES

EXAMPLES VIIIA–XA

The compounds of Examples VIIIA–XA were prepared in tetrahydrofuran using the procedure of Example IA only reacting 2.422 grams (0.01 mole) of beta(2,2,6,6-tetramethyl-4-piperidinylamino)propionic acid hydrazide with 0.01 mole of the appropriate anhydride in 50 ml of tetrahydrofuran. The product from 2-dodecen-1-ylsuccinic anhydride was isolated by stripping off the tetrahydrofuran on a rotating evaporator under reduced pressure. The other products were isolated by filtration and air drying. The infrared spectra (nujol mull) of the products were all consistent with the amic acid structure indicating that cyclization to the imide had not occurred. The results are summarized in Table III.

TABLE III

Reaction of N—(2,2,6,6-tetramethyl-4-piperidinylamino)-
propionic Acid Hydrazide in Tetrahydrofuran

| Ex. # | Anhydride | Anhydride (grams) | Yield (grams) | Color | m.p. °C. | Carbonyl Bands (cm$^{-1}$) | Intensity |
|---|---|---|---|---|---|---|---|
| VIIIA | 2-dodecen-1-yl-succinic | 2.66 | 5.2 | white | 108–111 | 1620 | strong |
| | | | | | | 1550 | strong |
| | | | | | | 1650 | medium |
| IXA | hexahydro-4-methyl-phthalic | 1.68 | 3.1 | white | 135–137 | 1615 | strong |
| | | | | | | 1545 | strong |
| XA | phthalic | 7.41 | 4.0 | white | 143–145 | 1615 | strong |

TABLE III-continued

Reaction of N—(2,2,6,6-tetramethyl-4-piperidinylamino)-
propionic Acid Hydrazide in Tetrahydrofuran

| Ex. # | Anhydride | Anhydride (grams) | Yield (grams) | Color | m.p. °C. | Carbonyl Bands (cm$^{-1}$) | Intensity |
|---|---|---|---|---|---|---|---|
| | | | | | | 1550 | strong |

EXAMPLE XI

Reaction of 2-Dodecylsuccinic Anhydride with N-(2,2,6,6-tetramethyl-4-piperidinyl)-N'-aminooxamide in Refluxing Xylene N-(2,2,6,6-tetramethyl-4-piperidinyl)-N'-(2-dodecylsuccinimido)-oxamide was prepared by slowly adding 24.2 grams (0.1 mole) of N-(2,2,6,6-tetramethyl-4-piperidinyl)-N'-aminooxamide to a solution of 26.8 grams (0.1 mole) dodecylsuccinic anhydride in 300 mls of refluxing xylene. After the addition was complete, the reaction was azeotroped 5 hours using a Dean Stark trap to remove the water of reaction. The reaction was cooled to room temperature and the product precipitated by stirring the reaction mixture into 500 mls of hexane. A greasy precipitate formed was very difficult to filter. The supernant solvent was decanted off and the wet precipitate transferred to a wide mouth flask and the solvent stripped off on a rotating evaporator under reduced pressure. The residue was scraped out of the flask, pulverized in a mortar with a pestle and air dried overnight. The dry powder weighed 38.7 grams, had a light straw color and had a melting range of 84°–87° C. An infrared scan (nujol mull) of the product contained carbonyl bands at 1725 cm$^{-1}$ and 1590 cm$^{-1}$. The infrared spectrum was consistent with the imide structure.

EXAMPLE XII

Reaction of 2-Octadecylsuccinic Anhydride with N-(2,2,6,6-tetramethyl-4-piperidinyl)-N'-aminooxamide in Refluxing Xylene N-(2,2,6,6-tetramethyl-4-piperidinyl)-N'-(2-octadecylsuccinimido)-oxamide was prepared by adding 24.2 grams (0.1 mole) of N-(2,2,6,6-tetramethyl-4-piperidinyl)-N'-aminooxamide to a hot solution (135°–140° C.) of 35.2 grams (0.1 mole) octadecylsuccinic anhydride in 300 mls xylene using the procedure described in Example XI. After azeotroping 3 hours, the xylene was stripped off on a rotating evaporator under reduced pressure using a heat gun. The yellow viscous residue weighed 58.0 grams and solidified to a white solid upon cooling (m.p. 65°–68° C.). An infrared scan (nujol mull) of the product contained a moderate carbonyl band at 1720 cm$^{-1}$ and a moderate broad band at 1585 cm$^{-1}$. The infrared spectrum was consistent with the imide structure.

EXAMPLE XIII

Reaction of Hexahydro-4-methylphthalic Anhydride with N-(2,2,6,6-tetramethyl-4-piperidinyl)-N'-aminosuccinamide in Refluxing Xylene Into a 250 ml 3-neck flask was added 4.2 grams (0.025 mol) of hexahydro-4-methylphthalic anhydride and 100 mls xylene. The flask was equipped as in Example IB. The mixture was heated in an oil bath to reflux and 6.75 grams (0.025 mole) of N-(2,2,6,6-tetramethyl-4-piperidinyl)-N'-aminosuccinimide were added in increments over ½ hour. The reaction mixture was azeotroped for 2 hours, cooled to 50° C. and the reaction mixture transferred to a 500 ml round bottom flask and the xylene was stripped off on a rotating evaporator under reduced pressure. The residue was a light yellow viscous liquid which solidified on cooling. After solidifying, the residue was scraped out of the flask and pulverized into an off-white powder in a mortar with a pestle. The infrared spectrum of the product (in CH$_2$Cl$_2$) had strong sharp carbonyl bands at 1720 cm$^{-1}$ and 1695 cm$^{-1}$ and moderate broad bands at 1640 cm$^{-1}$ and 1520 cm$^{-1}$. The starting anhydride band at 1780 cm$^{-1}$ was completely gone. The infrared spectrum of the product was consistent with the imide structure indicating that the amic acid had predominantly cyclized to the imide under the reaction conditions. DSC and FTIR scans before and after heating to 200° C. also confirmed that the amic acid had cyclized completely under the reaction conditions.

EXAMPLES XIV–XIX

Dry blends of Himont's Profax 6501 polypropylene and cyclic anhydride derivatives of hindered amine light stabilizers from Examples I, II, III and XIII and a small amount of a hindered phenol antioxidant (Irganox 1076) were prepared in a gallon polyethylene container (For composition see Table IV). The blends were shaken well to insure a good dispersion of the additives in the polypropylene. The blends were then extruded on a Brabender Prep Center Extruder Model No. 1340 having a 1¼ inch screw diameter with a length to diameter ratio of 25:1. The extruder was operated at a screw speed of 20 RPM and all the heating zones were controlled at 220° C.

The first 100 grams of extrudate were used to purge out the extruder and were discarded. The remaining extrudate was air-cooled and pelletized. When the amic acid derivatives were used, the extrudate was partially foamed due to water evolved during the cyclization of the amic acid to the imide.

The pelletized extrudate was let down with more polypropylene (approximately 4 parts polypropylene to 1 part masterbatch—see Table IV) and enough Irganox 1076 to provide a 0.25% concentration. The blends were shaken well and reextruded at 220° C. and a screw speed of 30 RPM. None of the extrudates were foamed indicating that imidization of any amic acid derivatives to the corresponding imide derivatives occurred during the first extrusion. The extrudates were cooled and pelletized. The concentration of the 2,2,6,6-tetramethyl-4-piperidyl group in the composition was in the range of 0.25–0.35%.

The final compositions were injection molded in a Newbury 25 ton injection molding machine at 400° F. into 7⅜"×¾"×⅛" tensile bars.

Samples of the masterbatch compositions of Example XIV–XIX were dissolved in hot xylene. Infrared scans of the xylene solutions contained the characteristic imide bands regardless of whether the starting HALS adduct was the amic acid or the imide derivative indicating that the amic acids cyclized to the imides during the first extrusion.

XIII and optionally a small amount of an antioxidant were prepared in a polyethylene container (For composition see Table V). The blends were shaken well to insure a uniform dispersion of the additives in the poly-

TABLE IV

EXTRUSION OF POLYPROPYLENE (PP) WITH HALS DERIVATIVES OF CYCLIC ANHYDRIDES

| EXAMPLE # | HALS DERIV | GRAMS HALS | PP GRAMS | IRGANOX 1076 GRAMS | YIELD | ADDITIONAL PP GRAMS | ADDITIONAL IRGANOX 1010 GRAMS | FINAL YIELD | APPROX HALS CONC* |
|---|---|---|---|---|---|---|---|---|---|
| XIV | IA | 15.0 | 285 | 0.75 | 265 | 1065 | 3.3 | 1197 | 0.31 |
| XV | IB | 12.0 | 228 | 0.60 | 190 | 760 | 2.4 | 830 | 0.35 |
| XVI | IIA | 10.5 | 285 | 0.75 | 276 | 1104 | 3.5 | 1292 | 0.30 |
| XVII | IIB | 8.4 | 228 | 0.60 | 293 | 1172 | 3.7 | 1360 | 0.25 |
| XVIII | IIIA | 12.0 | 285 | 0.75 | 279 | 1116 | 3.5 | 1275 | 1.29 |
| XIX | IIIB | 9.6 | 228 | 0.60 | 265 | 1060 | 3.3 | 1002 | 1.26 |
| C-1 | | | | | | 1000 | 2.5 | 860 | 0.0 |
| C-2 | T-770 | 10.0 | 1000 | 2.5 | 874 | 874 | 4.4 | 1530 | 0.29 |

T-770 = TINUVIN 770 (CIBA-GEIGY)
* = CONCENTRATION OF 2,2,6,6-TETRAMETHYL-4-PIPERIDINYL GROUPS IN FINAL

EXAMPLE XX

Reaction of Hexahydro-4-methylphthalic Anhydride with N-(2,2,6,6-tetramethyl-4-piperidinyl)-N'-aminooxamide in Molten Polypropylene A blend of 10.3 grams (0.042 mole) of N-(2,2,6,6-tetramethyl-4-piperidinyl)-N'-aminooxamide, 7.1 grams (0.042 mole) of hexahydro-4-methylphthalic anhydride, 1 gram Irganox 1076 and 380 grams of Himont's Profax 6501 polypropylene was prepared in a polyethylene container. The blend was shaken well to insure a good dispersion of the additives in the polypropylene. The blend was then extruded on a Brabender Prep Center Extruder as in Examples XIII–XIX, The extrudate was partially foamed and water vapor was evolved at the die face. The first 100 grams of extrudate were used to purge out the extruder and were discarded. The remaining extrudate was air-cooled and pelletized.

The pelletized extrudate was let down with more polypropylene as in Examples XIV–XIX and reextruded at 220° C. The extrudate was pelletized and injection molded as in Examples XIV–XIX. The concentration of the 2,2,6,6-tetra-methyl-4-piperidinyl group in the final composition was approximately 0.3% and the concentration of the Irganox 1076 was approximately 0.25%.

propylene. The blends were then extruded on a Brabender Prep Canter Extruder at 220° C. and a screw speed of 30 RPM as in Example XIV–XIX. The first 100 grams of extrudate were used to purge out the extruder and were discarded. The remaining extrudate was air cooled and pelletized.

The pelletized extrudate was injection molded as in Examples XIV–XIX. The concentration of the 2,2,6,6-tetramethyl-4-piperidinyl group in the final composition was approximately 0.3%.

EXAMPLE XXVI

Conversion of Amic Acids to Imides in the DSC

Samples from Examples 1A-XA were heated in a differential scanning calorimeter (Perkin-Elmer 7 Series Thermal Analysis System) under a nitrogen purge at a rate of 20° C./minute. An endothermic peak was generated upon heating the various amic acids. During the heating period, the onset of the endotherm, the temperature of the endotherm peak and the temperature where the endotherm died out were all noted. After the endotherm ceased, the heating was stopped, the sample cooled and an infrared spectrum was run on the residue. The infrared scan of the heated material was compared with the infrared scan of the starting amic acids. In all cases the strong carbonyl bands of the amic acids in the 1610–1660 cm$^{-1}$ region were converted to imide bands

TABLE V

EXTRUSION OF POLYPROPYLENE WITH HALS DERIVATIVES OF CYCLIC ANHYDRIDES

| EXAMPLE # | HALS DERIV | GRAMS | ANTIOXIDANT | GRAMS | POLYPROPYLENE GRAMS |
|---|---|---|---|---|---|
| XXI | XI | 4.2 | — | — | 390 |
| XXII | XI | 4.2 | IRGANOX 1076 | 1.0 | 390 |
| XXIII | IIIB | 3.3 | — | — | 390 |
| XXIV | IIIB | 3.3 | IRGANOX 1076 | 1.0 | 390 |
| XXV | XIII | 1.9 | IRGAPHOS 168 | 0.3 | 110 |

EXAMPLES XXI–XXV

Dry blends of Himont's Profax 6501 polypropylene and HALS derivatives from Examples IIIB, XI and in the 1700–1740 cm$^{-1}$ region. The results are summarized in Table VI.

TABLE VI

Conversions of Amic Acids to Imides in the DSC

| | ENDOTHERM °C. | | | DOMINANT CARBONYL BANDS IN IR SPECTRA | |
|---|---|---|---|---|---|
| Ex. # | ONSET | PEAK | END | BEFORE HEATING | AFTER HEATING |
| IA | 145 | 194 | 205 | 1610–1635 (s) | 1740 (s) |

TABLE VI-continued

Conversions of Amic Acids to Imides in the DSC

| Ex. # | ENDOTHERM °C. | | | DOMINANT CARBONYL BANDS IN IR SPECTRA | |
|---|---|---|---|---|---|
| | ONSET | PEAK | END | BEFORE HEATING | AFTER HEATING |
| IIA | 192 | 233 | 250 | 1520–1540 (m)<br>1650 (s) | 1080 (s)<br>1710 (s) |
| IIIA | 142 | 181 | 194 | 1570–1610 (m)<br>1620 (s) | 1670 (vs)<br>1740 (vs) |
| IVA | 108 | 134 | 156 | 1640 (s)<br>1660 (s) | 1680 (s)<br>1735 (vs) |
| VA | 235 | 256 | 265 | 1630 (s)<br>1630 (s) | 1680 (s)<br>1740 (s) |
| VIA | 177 | 223 | 250 | 1670 (w)<br>1640 (s) | 1665 (s)<br>1740 (m) |
| VIIA | 155 | 192 | 207 | 1500–1530 (m)<br>1645 (s) | 1700 (s)<br>1740 (s) |
| VIIIA | 130 | 151 | 176 | 1620 (w)<br>1545 (m)<br>1650 (m) | 1680 (s)<br>1735 (vs) |
| IXA | 127 | 154 | 175 | 1620 (s)<br>1615 (s) | 1700 (m)<br>1740 (vs) |
| XA | 128 | 155 | 180 | 1545 (s)<br>1615 (s)<br>1550 (s) | 1705 (w)<br>1740 (vs)<br>1710 (m) |

EXAMPLE XXVII

Evaluation of the HALS Derivatives in the Stabilization of Polypropylene

The tensile bars from Examples XIV–XXV were placed in a QUV Accelerated Weathering Tester (Q Panel Company) for various exposure times. The QUV operated with an 8 hour light cycle (UV-B) at 60° C. and a 4 hour condensation cycle at 50° C. Samples were placed in the QUV and withdrawn at approximately the same time each day during the condensation cycle. Samples withdrawn from the QUV were evaluated for change in yellowing (ΔE) on a Colorgard System/05 (Pacific Scientific) colorimeter. Control samples without any UV stabilizer or additional antioxidant (unextruded) as well as extruded controls containing Irganox 1076 and Irganox 1076 with Tinuvin 770 were included in the study.

After measuring the color, the tensile bars were pulled on an Instron and the % elongation determined. By comparing the % elongation of the unexposed samples with the exposed samples, the % retention of elongation was calculated for the various exposure periods. If the tensile bar snapped with essentially no elongation, the test result was considered a brittle break (BB). The first appearance of crazing, cracking or haziness over the exposed surface was also noted. The results are summarized in Table VII.

TABLE VII

STABILIZATION OF POLYPROPYLENE WITH POLYMER BOUND HALS

| EXAMPLE OF RESIN | INITIAL | | 3 DAYS | | | 5 DAYS | | | 7 DAYS | | | 10 DAYS | | |
|---|---|---|---|---|---|---|---|---|---|---|---|---|---|---|
| | % EL | YID | % EL | % RE | DE | % EL | % RE | DE | % EL | % RE | DE | % EL | % RE | DE |
| XIII | 206 | 22.6 | 75 | 36 | 2.2 | 75 | 36 | 2.2 | 88 | 42 | 2.1 | 88 | 42 | 2.7 |
| XIV | 125 | 20.7 | 88 | 70 | 1.4 | 63 | 50 | 1.4 | 38 | 30 | 1.6 | 63 | 50 | 2.1 |
| XV | 150 | 47.2 | 88 | 58 | 2.1 | 88 | 58 | 2.6 | 56 | 38 | 2.9 | 100 | 67 | 3.5 |
| XVI | 100 | 40.2 | 100 | 100 | 1.5 | 63 | 63 | 1.6 | 50 | 50 | 1.6 | 63 | 63 | 1.9 |
| XVII | 188 | 22.9 | 88 | 47 | 2.1 | 75 | 40 | 1.3 | 75 | 40 | 2.3 | 88 | 47 | 2.8 |
| XVIII | 88 | 22.1 | 50 | 57 | 1.7 | 50 | 57 | 1.9 | 25 | 29 | 1.7 | 50 | 57 | 1.9 |
| XIX | 125 | 37.7 | 50 | 40 | 1.6 | 19 | 15 | 1.5 | 44 | 35 | 2.0 | | | |
| XX | 119 | 45.8 | 88 | 74 | 2.5 | 50 | 42 | 2.4 | 56 | 47 | 2.5 | | | |
| XXI | 106 | 18.7 | 69 | 65 | 1.4 | 50 | 47 | 0.9 | 50 | 47 | 0.6 | | | 0.7 |
| XXII | 125 | 20.3 | 88 | 70 | 0.8 | 50 | 40 | 1.0 | 38 | 30 | 0.9 | | | 1.2 |
| XXIII | 113 | 17.8 | 81 | 72 | 0.8 | 44 | 39 | 1.3 | 50 | 47 | 1.2 | | | 1.3 |
| XXIV | 100 | 20.7 | 69 | 69 | 0.7 | 31 | 31 | 1.1 | 31 | 31 | 1.2 | 44 | 44 | 0.7 |
| XXV | 181 | 29.1 | 69 | 38 | 5.3 | | | | | | | | | |
| C-1 | 113 | 17.1 | 63 | 56 | 0.5 | BB | | 1.0 | BB | | 1.0 | BB | | 3.3* |
| C-2 | 125 | 19.8 | 113 | 90 | 2.1 | 56 | 50 | 2.9 | 38 | 30 | 4.3 | 19 | 50 | 5.4 |
| C-3 | 163 | 18.3 | 13 | 8 | 3.0* | BB | | 3.4* | | | | | | |
| C-4 | 100 | 17.7 | 6 | 6 | 4.0* | BB | | 4.2 | | | | | | |

| EXAMPLE OF RESIN | 15 DAYS | | | 20 DAYS | | | 25 DAYS | | | 30 DAYS | | | DAYS TO C & C |
|---|---|---|---|---|---|---|---|---|---|---|---|---|---|
| | % EL | % RE | DE | % EL | % RE | DE | % EL | % RE | DE | % EL | % RE | DE | |
| XIII | 63 | 42 | 2.7 | 35 | 17 | 2.6 | | | | | | 3.9 | 17 |
| XIV | 88 | 70 | 1.9 | 43 | 35 | 2.2 | 44 | 35 | 2.1 | | | 2.4 | >30 |
| XV | 81 | 54 | 2.6 | 87 | 58 | 2.3 | | | | | | 2.4 | >30 |
| XVI | 44 | 44 | 2.2 | 81 | 81 | 1.8 | 50 | 50 | 1.3 | | | 2.2 | >30 |
| XVII | 75 | 40 | 2.6 | 19 | 10 | 2.8 | | | | | | 2.8 | >30 |
| XVIII | 25 | 29 | 1.8 | 19 | 21 | 2.2 | 18 | 21 | 1.9 | | | 2.6 | >30 |
| XIX | 19 | 15 | 2.3 | 19 | 15 | 3.0 | 19 | 15 | 2.6 | 12 | 10 | 2.3 | >30 |
| XX | 44 | 37 | 2.2 | 38 | 32 | 2.4 | 31 | 26 | 2.2 | 13 | 11 | 2.4 | >30 |
| XXI | | | | 50 | 47 | 1.6 | 38 | 35 | 1.8 | | | 2.2 | >40 |

TABLE VII-continued
STABILIZATION OF POLYPROPYLENE WITH POLYMER BOUND HALS

| | | | | | | | | | | | |
|---|---|---|---|---|---|---|---|---|---|---|---|
| XXII | | | | 44 | 35 | 1.3 | 38 | 30 | 1.5 | 1.7 | >40 |
| XXIII | | | | 50 | 44 | 1.6 | 44 | 39 | 2.3 | 2.0 | >40 |
| XXIV | 38 | 38 | 0.9 | 25 | 25 | 2.0 | 31 | 31 | 3.1 | | >25 <30 |
| XXV | 25 | 14 | 3.9 | 19 | 10 | 3.1 | | | | | >20 |
| C-1 | | | | | | | | | | | >10 |
| C-2 | 25 | 20 | 6.5 | BB | | 6.6 | BB | | 7.6 | BB | 8.9 | >40 <45 |
| C-3 | | | | | | | | | | | <3 |
| C-4 | | | | | | | | | | | <3 |

LEGEND:
% EL = PERCENT ELONGATION
% RE = PERCENT RETAINED ELONGATION
DE = TOTAL COLOR CHANGE (DELTA E)
C & C = CRACKING AND CRAZING
BB = BRITTLE BREAK OCCURRED
C3 = UNSTABLIZED POLYPROPYLENE EXTRUDED TWICE
C4 = UNSTABLIZED POLYPROPYLENE EXTRUDED ONCE
* = SAMPLE CRAZED AND CHALKY

What is claimed:
1. A composition of the following structure:

$$\begin{array}{c} R^2-CH_2 \quad CH_3 \\ \diagdown \diagup \\ C-CH-R^2 \\ R^1-N \quad C-Y-R \\ C-CH_2 \quad R^3 \\ \diagup \diagdown \\ R^2-CH_2 \quad CH_3 \end{array}$$

where R is selected from $$-N\begin{array}{c}C=O\\ \diagdown \\ \diagup \\ C=O\end{array}X \quad \text{and} \quad -NH-\overset{O}{\overset{\|}{C}}-X-\overset{O}{\overset{\|}{C}}OH$$

and X is selected from 1,2-aryl diradical of 6–12 carbons, 1,8-naphthyl diradical of 10–14 carbons, aryl-alkyl diradical of 7–13 carbons, saturated or unsaturated alkylene, cycloalkylene or bicycloalkylene diradical of 2–20 carbons which may be optionally substituted with carboxy, alkyl of 1–40 carbons, alkylthio of 1–18 carbons, alkoxy of 1–18 carbons, alkenyl of 2–40 carbons, arylthio of 6–20 carbons, aryl of 6–16 carbons, aralkyl of 7–17 carbons, aryloxy of 6–16 carbons, aralkylthio of 7–20 carbons or alkoxycarbonylalkylthio of 3–30 carbons.

$R^1$ is hydrogen, oxyl, hydroxyl, alkyl of 1–20 carbons, alkenyl or alkynyl of 3–8 carbons, aralkyl of 7–12 carbons, aliphatic acyl of 1–10 carbons, aromatic acyl of 7–13 carbons, alkoxycarbonyl of 2–9 carbons, aryloxycarbonyl of 7–15 carbons, alkyl, aryl, cycloalkyl or aralkyl substituted carbamoyl of 2–13 carbons, hydroxyalkyl of 1–5 carbons, 2-cyanoethyl, epoxyalkyl of 3–10 carbons or a polyalkylene oxide group of 4 to 30 carbons, $R^2$ is hydrogen or alkyl of 1–4 carbons, $R^3$ is hydrogen, hydroxyl or alkoxy of 1–4 carbons, when $R^3$ is hydrogen, Y is a divalent radical selected from —Z—$R^4$—C(=O)—N($R^5$)—, —Z—C(=O)—N($R^5$)—, —Z—C(=O)—$R^6$—C(=O)—N($R^5$)—, —$R^4$—C(=O)—N($R^5$)—, —C(=O)—N($R^5$)—, Z is —O—, —N($R^7$)— or —N($R^9$)—$R^8$—N($R^9$)—, when $R^3$ is hydroxyl or alkoxy, Y is a divalent radical selected from —$R^4$—C(=O)—N($R^5$)—, —C(=O)—N($R^5$)—, $R^4$ is an alkylene diradical of 1–4 carbons, $R^5$ is hydrogen, primary or secondary alkyl of 1–8 carbons, aralkyl of 7–12 carbons or cycloalkyl of 5–20 carbons, $R^6$ is a direct bond, alkylene of 1–14 carbons, oxydialkylene of 4–10 carbons, thiodialkylene of 4–10 carbons, alkenylene of 2–20 carbons, o-, m- or p-phenylene and $R^6$ may be optionally substituted with lower alkyl or alkoxy of 1–8 carbons, hydroxy, bromine, chlorine, mercapto or lower alkylmercapto of 1–8 carbons, $R^7$ is hydrogen, alkyl of 1 to 10 carbons, aryl of 6 to 12 carbons, aralkyl of 7–12 carbons, cycloalkyl of 5–12 carbons, 2-cyanoethyl or a radical of the formula $$\begin{array}{c} R^2-CH_2 \quad CH_3 \\ \diagdown \diagup \\ C-CH-R^2 \\ R^1-N \quad CH- \\ C-CH_2 \\ \diagup \diagdown \\ R^2-CH_2 \quad CH_3 \end{array}$$

and $R^8$ is alkylene of 2–12 carbons and $R^9$ is hydrogen, alkyl of 1–10 carbons, aryl of 6–12 carbons, aralkyl of 7–12 carbons or cycloalkyl of 5–12 carbons.

2. The composition of claim 1 where X is selected from o-phenylene, 1,2-ethylene, 1,3-propylene, 1,2-cyclohexylene, 4-methyl-1,2-cyclohexylene, 1,2-cyclohex-4-enylene, norborn-5-enylene, 2,3-norbornylene 2,3-bicyclo[2.2.2]oct-5-enylene, 2,3-bicyclo[2.2.2]octylene, alkyl, alkenyl, alkylthio, arylthio or aralkylthio of 1–30 carbons, substituted 1,2-ethylene or 2,3-norbornylene, $R^1$ is hydrogen, methyl, acetyl, benzoyl, 2-hydroxyethyl or benzyl, $R^2$ is hydrogen or methyl, $R^3$ is hydrogen, Y is selected from —Z—$R^4$—C(=O)—N($R^5$)—, —Z—C(=O)—$R^6$—C(=O)—N($R^5$)—, and Z is —N($R^7$)—, $R^4$ is —(CH$_2$)$_b$, $R^5$ is hydrogen, $R^6$ is a direct bond or alkylene of 1–4 carbons, b is 1 or 2 and $R^7$ is hydrogen or 2,2,6,6-tetramethyl-4-piperidinyl.

3. The composition of claim 2 where X is o-phenylene, alkyl or alkenyl substituted 1,2-ethylene of 1–20 carbons, 1,3-propylene, 1,2-cyclohexylene, 4-methyl- 1,2-cyclohexylene or 2,3-norborn-5-enylene; $R^1$ is hydrogen or methyl, $R^2$, is hydrogen, and $R^6$ is a direct bond or alkylene of 2 or 4 carbons.

4. The composition of claim 3 where X is dodecyl-1,2-ethylene, dodecen-1-yl-1,2-ethylene, octadecyl-1,2-ethylene, octadecen-1-yl-1,2-ethylene, 1,3-propylene, 4-methyl-1,2-cyclohexylene, 5-methyl-2,3-norbornylene, 1,2-ethylene or o-phenylene, Y is the diradical —Z—C(=O)—$R^6$—C(=O)—N($R^5$)—, $R^1$, $R^5$ and $R^7$ are hydrogen and $R^6$ is a direct bond or 1,2-ethylene.

5. The composition of claim 4 where R is

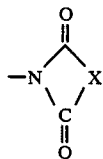

and $R^6$ is a direct bond.

6. The composition of claim 5 where X is dodecyl-1,2-ethylene.

7. The composition of claim 5 where X is octadecyl-1,2-ethylene.

8. The composition of claim 5 where X is 4-methyl-1,2-cyclohexylene.

9. The composition of claim 5 where X is dodecen-1-yl-1,2-ethylene.

10. The composition of claim 5 where X is 1,3-propylene.

11. The composition of claim 4 where X is 4-methyl-1,2-cyclohexylene and $R^6$ is 1,2-ethylene.

12. The composition of claim 11 where R is

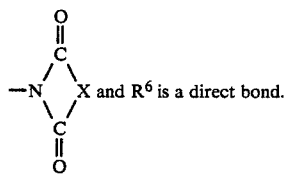

13. The composition of claim 3 where X is dodecen-1-yl-1,2-ethylene, 4-methyl-1,2-cyclohexylene or o-phenylene, Y is the diradical —Z—$R^4$—C(=O)—N($R^5$)—, Z is —N($R^7$)—, $R^1$, $R^5$ and $R^7$ are hydrogen and $R^4$ is 1,2-ethylene.

14. The composition of claim 13 where R is

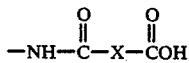

and X is 4-methyl-1,2-cyclohexylene.

15. The process of preparing the composition of claim 1 by reacting a hydrazido functionalized polyalkylpiperidine of the following structure

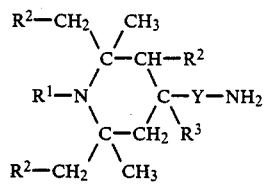

with a cyclic anhydride of the following structure

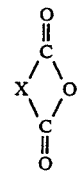

in approximately equal molar amounts, either neat, in an inert solvent or in an inert polymeric composition at a temperature range from about 125°–300° C.

16. The process of claim 15 where the product formed is an amic acid containing an acylamino substituent on the amide nitrogen of the amic acid, heating said product in a melt blending step to a temperature from about 100°–230° C. to cyclize the amic acid to N-(acylamino)imide.

17. The process of claim 16 where the melt blending step is carried out in the presence of an inert polymeric composition above the softening point of the polymeric composition.

18. A stabilized synthetic polymer composition comprising a synthetic polymer and the composition of claim 1 in an amount effective to stabilize the synthetic polymer against degradative effects of heat or light.

19. The stabilized synthetic polymer composition of claim 18 wherein the synthetic polymer is a polyolefin, an acrylic polymer, a styrene polymer, a rubber modified styrene polymer, a polyphenylene ether, a polycarbonate, a polyamide or mixtures thereof.

20. A stabilized polypropylene composition comprising polypropylene and the composition of claim 6 in an amount effective to stabilize the polypropylene against degradative effects of heat or light.

21. A stabilized polypropylene composition comprising polypropylene and the composition of claim 8 in an amount effective to stabilize the polypropylene against degradative effects of heat or light.

22. A stabilized polypropylene composition comprising polypropylene and the composition of claim 10 in an amount effective to stabilize the polypropylene against degradative effects of heat or light.

23. A stabilized polypropylene composition comprising polypropylene and the composition of claim 11 in an amount effective to stabilize the polypropylene against degradative effects of heat or light.

* * * * *